(12) United States Patent
Bondurant et al.

(10) Patent No.: US 9,385,448 B2
(45) Date of Patent: Jul. 5, 2016

(54) ELECTRICAL CONNECTION VIA FASTENER HOLE

(71) Applicant: Quest Integrated, Inc., Kent, WA (US)

(72) Inventors: Phillip D. Bondurant, Covington, WA (US); Giovanni Nino, Issaquah, WA (US); David W. Rook, Kent, WA (US); Anthony Mactutis, Auburn, WA (US); David Bothell, Lake Tapps, WA (US)

(73) Assignee: Quest Integrated, LLC, Kent, WA (US)

( * ) Notice: Subject to any disclaimer, the term of this patent is extended or adjusted under 35 U.S.C. 154(b) by 150 days.

(21) Appl. No.: 13/956,331

(22) Filed: Jul. 31, 2013

(65) Prior Publication Data

US 2015/0097590 A1    Apr. 9, 2015

Related U.S. Application Data

(60) Provisional application No. 61/677,887, filed on Jul. 31, 2012.

(51) Int. Cl.
| | |
|---|---|
| *G01R 19/00* | (2006.01) |
| *H01R 11/00* | (2006.01) |
| *G01N 29/22* | (2006.01) |
| *G01N 17/04* | (2006.01) |
| *G01R 1/04* | (2006.01) |
| *G01N 1/00* | (2006.01) |
| *F16B 1/00* | (2006.01) |

(52) U.S. Cl.
CPC ............... *H01R 11/00* (2013.01); *G01N 17/04* (2013.01); *G01N 29/223* (2013.01); *G01R 1/0416* (2013.01); *F16B 2001/0064* (2013.01); *G01N 1/00* (2013.01); *G01N 2201/00* (2013.01); *G01N 2203/00* (2013.01); *G01N 2291/0289* (2013.01); *G01N 2291/2691* (2013.01); *G01N 2291/2694* (2013.01)

(58) Field of Classification Search
CPC .. G01N 1/00; G01N 2201/00; G01N 2203/00
See application file for complete search history.

(56) References Cited

U.S. PATENT DOCUMENTS

| | | | |
|---|---|---|---|
| 4,454,006 A | 6/1984 | Hausler | |
| 5,571,955 A | 11/1996 | Beavers | |
| 6,490,927 B2 * | 12/2002 | Braunling et al. | 73/597 |
| 7,528,598 B2 | 5/2009 | Goldfine | |
| 7,886,624 B1 * | 2/2011 | Mayeaux | G01N 1/2035 73/866.5 |
| 2006/0162432 A1 | 7/2006 | Jaralla | |
| 2009/0131769 A1 * | 5/2009 | Leach et al. | 600/309 |
| 2009/0274578 A1 * | 11/2009 | Hicks | G01N 17/02 422/53 |

(Continued)

OTHER PUBLICATIONS

International Search Report and Written Opinion mailed Oct. 28, 2013, in International Application No. PCT/US2013/053101, filed Jul. 31, 2013, 13 pages.

*Primary Examiner* — Huy Q Phan
*Assistant Examiner* — Temilade Rhodes-Vivour
(74) *Attorney, Agent, or Firm* — Christensen O'Connor Johnson Kindness PLLC (57) ABSTRACT

The systems, apparatus, and methods disclosed herein provide access to systems located within a closed structure, such that the systems are traditionally difficult for humans to access. Exemplary structures include an engine compartment, airplane wing, or fuselage. This access allows a system located within the structure to be electrically coupled with an electrical I/O device located outside the structure. Access to a system located within the closed structure is provided by way of a hole.

26 Claims, 10 Drawing Sheets

(56) References Cited

U.S. PATENT DOCUMENTS

2011/0262695 A1\* 10/2011 Lee et al. .................... 428/131
2012/0052708 A1\* 3/2012 Herring ........................ 439/345
2012/0187000 A1\* 7/2012 Kahn ................. G01N 27/3335
  205/782

\* cited by examiner

ELECTRICAL CONNECTION VIA FASTENER HOLE

CROSS-REFERENCE TO RELATED APPLICATION

This application claims the benefit of U.S. Provisional Patent Application No. 61/677,887, filed Jul. 31, 2012, the disclosure of which is incorporated by reference herein in its entirety.

STATEMENT OF GOVERNMENT LICENSE RIGHTS

This invention was made with Government support under Contract No. FA8501-09-C-0029 awarded by the U.S. Air Force. The Government has certain rights in the invention.

BACKGROUND

Corrosion of structural elements, such as bolts, fasteners, and beams is problematic because it reduces the strength and effectiveness of the structural element. Corrosion of structural supports is often not readily observable making it difficult to detect. Left undetected, corrosion can damage a structure thereby causing reduced reliability or failure.

Maintaining structural integrity is especially important in aerospace applications. Corrosion has been found on the inboard trailing edges of some types of airplane wings. The inboard area of an airplane wing is not readily viewable or accessible by a human. Current methods of inspecting the inboard area require a complex process involving the removal of the upper wing skin and its associated fasteners. Executing this task is time consuming and expensive, and it may generate more damage to the wing structure than the actual corrosion.

Sensing systems may be embedded within a wing or other host structure within an airplane to sense for corrosion or other undesirable properties. Installing a sensing system may also require significant electrical system modifications and rewiring. These systems add considerable weight and can be a burden on the structures the systems were installed to protect. In addition, it can be difficult for a technician to access an inner space of a wing and other tight spaces in and around an aircraft to interact with such a system. These sensing systems also require maintenance to keep the on-board electronics in proper working order.

SUMMARY

In one aspect, an electrical connection plug is provided. In one embodiment, the electrical connection plug is sized and configured to mate with, and thereby form an electrical connection with, one or more electrodes disposed within an interior space of a closed structure by way of insertion through a hole in the closed structure configured to retain a fastener.

In another aspect, a method of forming an electrical connection with one or more electrodes disposed within a closed structure is provided. In one embodiment, the electrodes are disposed in an interior space of the closed structure adjacent a hole in the closed structure configured to retain a fastener, the method comprising the step of inserting an electrical connection plug sized and configured to mate with the one or more electrodes through the hole until the plug forms at least one electrical contact with at least one electrode.

In another aspect, corrosion sensor network configured to test a level of corrosion of a test piece is provided. In one embodiment, the corrosion sensor network includes at least one pair of sensing/acting transducers positioned with the test piece in between and interconnects connecting the at least one pair of sensing/acting transducers with an electrical I/O interface.

In another aspect, a system is provided. In one embodiment, the system includes a socket having one or more electrodes that are electrically coupleable to a first electronic device. The system also includes a plug that is electrically coupleable to an electronic I/O device. The socket is configured to mate exclusively through a hole with either the plug or a fastener. The socket and the plug are sized and configured to electrically couple the one or more electrodes through the plug when the socket and the plug are mated. The hole is configured to be covered when the socket is mated with the fastener. The socket is coupleable to a fastening system configured to join two surfaces of a structure when the socket is mated with the fastener.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

The systems, apparatus, and methods disclosed herein provide access to systems located within a closed structure, such that the systems are traditionally difficult for humans to access. Exemplary structures include an engine compartment, airplane wing, or fuselage. This access allows a system located within the structure to be electrically coupled with an electrical I/O device located outside the structure. Access to a system located within the closed structure is provided by way of a hole. In one configuration of the system, data may be obtained from the sensing system through the hole and provided to other systems, such as Structural Health Monitoring (SHM) systems for vehicles. If the hole is not needed for electrical coupling, a fastener may be utilized to provide structural support and protection. Although the disclosed systems, apparatus, and methods, are particularly useful in connection with aerospace or vehicle applications, the present disclosure may also be implemented in a wide range of applications where an existing fastener may provide access to a closed structure.

Figure 1:
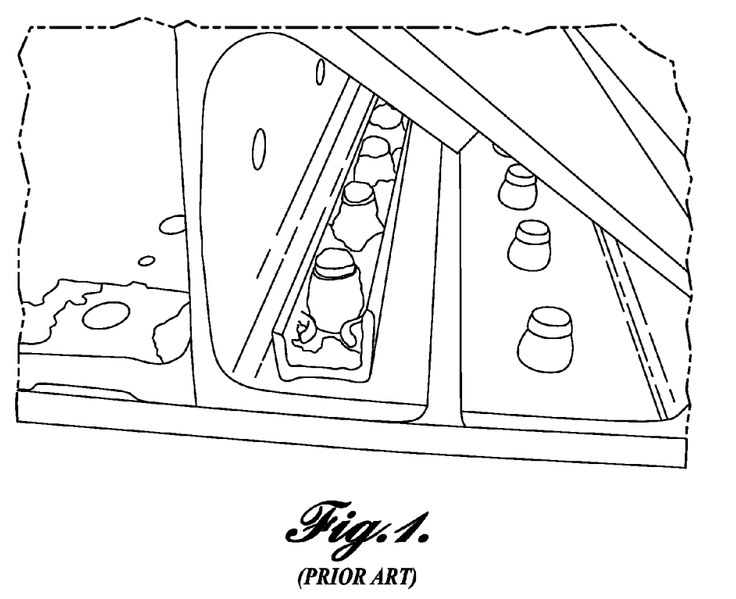
FIG. 1 is an internal view of a wing trailing edge assembly showing corrosion on a blot and socket.

FIG. 1 shows an inner portion of a prior art airplane wing fastening system where multiple fasteners are each mated to a matching socket. The sockets are positioned in a channel. A hole extends through two layers of material, a plate, and into a socket. The fastener extends from a side of the two layers that is opposite the socket, through the hole, and into the socket. Mating between the fastener and the socket joins together surfaces of the two layers, the plate, and the socket. As shown, corrosion is present around the sockets and the fastener. In some applications, such corrosion may not be viewable by a human without first disassembling surrounding adjacent structures. Disassembling adjacent structures to check for corrosion is time intensive, and it may actually generate damage to the structure.

Figure 2:
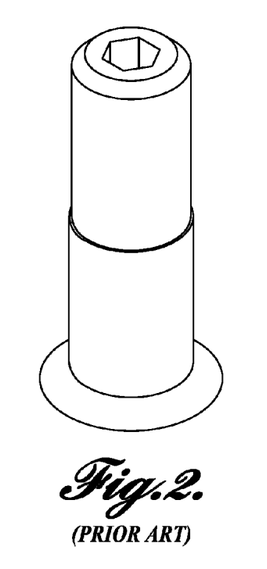
FIG. 2 is a front view of a prior art fastener.

FIG. 2 depicts a prior art fastener. The fastener has a cylindrical-shaped body defined between a first end and a second end, and it is comprised of a rigid metal material. The fastener is configured to mate with a socket (not shown). Mating between the socket and the fastener may be accomplished through a compatible socket and the fastener threading. For example, the fastener includes threads on a portion of its outer surface and the socket could include a nut with threads that are compatible with the fastener. When the fastener is mated with a socket, a joining force is generated. The joining force acts between a bottom surface of the socket and a bottom surface of the fastener. The fastener shown in FIG. 2 may compatible extent with portions of the systems described herein, such as the fastener hole connection system 100.

Figure 3:
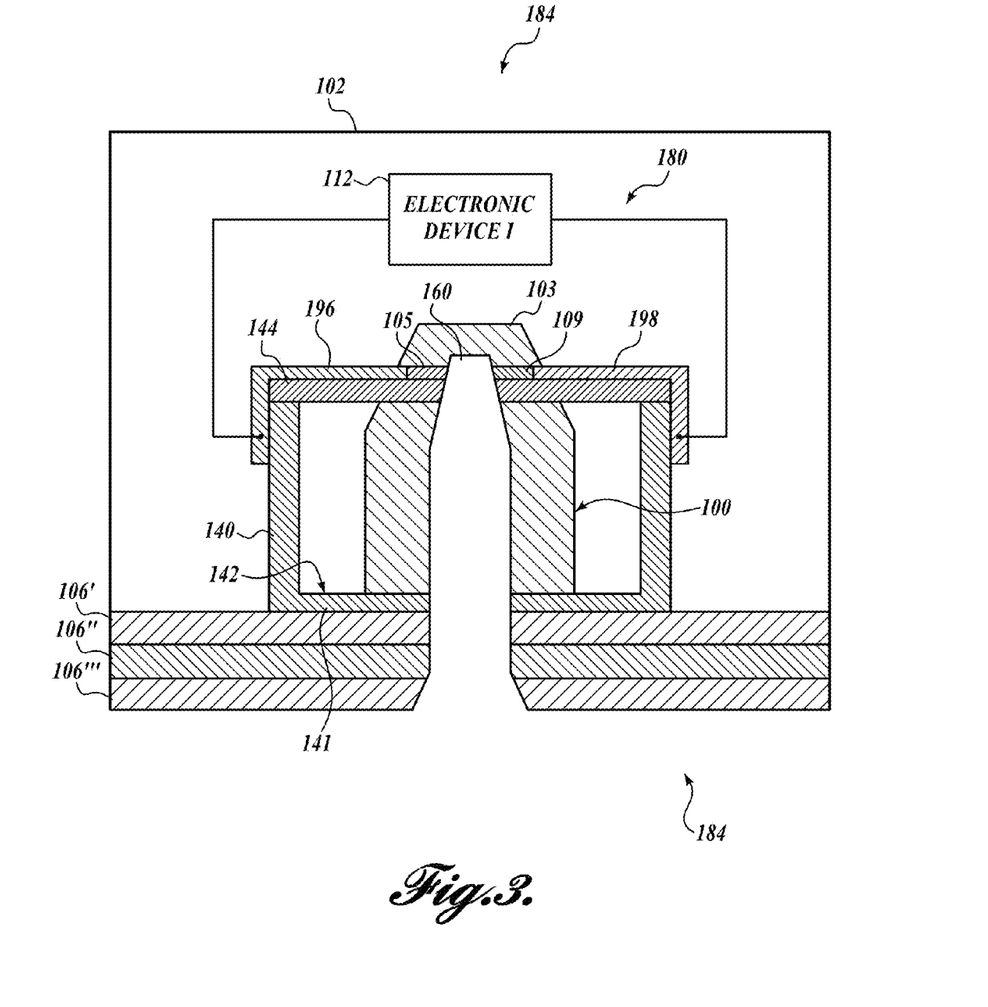
FIG. 3 is schematic diagram of a fastener hole connection system without a fastener or a plug inserted in accordance with one or more embodiments of the present disclosure.

FIG. 3 shows a fastener hole connection system 100 disposed within a closed structure 102. As used herein, the term "closed structure" refers to an enclosed structure that is not readily viewable or accessible by humans. The closed structure 102 may be accessed by a human if the human exerts a significant effort or uses a tool. The closed structure 102 includes an interior space 180. The closed surface 102 does not include space that may only be accessed with a finger or is uncomfortable for a person to access In one embodiment, the closed structure 102 includes a portion of an engine compartment of a vehicle that is uncomfortable for a human to access or may only be accessed with a finger. A person may access a portion of the vehicle within the closed structure 102, but such access is uncomfortable. An exterior space 184 is a space outside of the closed structure 102 and the interior space 180. The exterior space 184 may include an outer surface of the closed structure 102.

In a representative embodiment, the closed structure 102 includes a portion of an airplane wing assembly that includes a space surrounded by a physical structure. The wing assembly requires a tool to gain access through disassembly. The interior space 180 within the closed structure 102 includes one or more holes or sockets disposed within the closed structure 102. In one embodiment, the closed structure 102 is an aircraft fuselage assembly that is not readily accessed by a human without a tool and the interior space 180 is the space within the closed structure 102.

Still referring to FIG. 3, a channel 140 and the socket 103 may be disposed within the closed structure 102. The socket 103 may be placed on the channel 140. The channel 140 includes a bottom portion 141 that may have a flat shape. The channel 140 may be a gang channel, a nut plate, or a mounting plate. The socket 103 is disposed on a top surface 142 of the bottom portion 141 of the channel 140. The layers 106', 106", 106"' may be located below the channel 140. The channel 140, and the layers 106 include a hole 160 that passes from the socket to the exterior space 184. The socket 103 is positioned adjacent to the hole 160. The socket 103 may be secured to the channel 140 adjacent to the hole 160. In a representative embodiment, the hole 160 is perpendicular to one or more of the surfaces of the bottom portion 141 of the channel 140 and the first, second, or third layers 106', 106", 106"'. The hole 160 is configured to receive a fastener or a plug. In a representative embodiment, the socket 103 is configured to mate exclusively through the hole 160 with either a fastener or a plug.

The socket 103 includes one or more electrodes 105 or 109. Multiple electrode configurations of the one or more electrodes 105 or 109 are possible. For example, the socket 103 may have a linear, radial, or any other type of configuration such as the electrode orientations disclosed in FIGS. 8-10 and FIGS. 12-14. The specific layout of the electrodes 105 and 109 of the socket 103 may be determined based on available space, number of signals, diameter of a fastener hole, mechanical requirements, and electrical requirements, among other considerations.

The electrodes 105 and 109 may be electrically coupleable to a first electronic device 112. The first electronic device 112 may be located within the closed structure 102. The first electronic device 112 may include any known or future developed analog or digital circuitry, such as one or more of the following and combinations thereof: an embedded system, a network, a sensor, a storage device, a power supply, a switching device, and/or one or more control elements. A control element may include a microcontroller or microcomputer. The components of the first electronic device 112 may be electrically coupled to each other or may be electrically distinct. The first electronic device 112 may include a sensor network. In one embodiment, the first electronic device 112 includes a temperature sensor.

The first electronic device 112 may include an excitation source device. The excitation source device is any suitable device for generating one or more of the following excitations: electrical, mechanical, thermal, magnetic, optical, electromagnetic, acoustical, ultrasonic, and combinations thereof. In one embodiment, the excitation source may be one or more signal generators. The first electronic device 112 may also include a receiving device. The receiving device is a suitable device for receiving or detecting one of the following excitations: electrical, mechanical, thermal, magnetic, optical, electromagnetic, acoustical, ultrasonic, and combinations thereof. The receiving device may include one or more sensors, transducers, data acquisition units, and/or data processing units. In one embodiment, the receiving device may convert the received excitation into an electrical signal.

In a representative embodiment, the first electronic device 112 includes one or more pairs of piezoelectric transducers. Representative transducers include piezoelectric and electromagnetic acoustic (EMAT) transducers, although any transducer known to those of skill in the art is compatible with the provided embodiments. A first piezoelectric transducer is configured as a driving transducer and a second piezoelectric transducer is configured as a sensing transducer. In one embodiment, the signal generated by the first transducer indicates a corrosion level of a test piece located between the pair of transducers. The test piece is any piece, portion, or specimen of any material, used for testing or determining qualities and properties. The test piece may include or be located within the closed structure 102.

The electrodes 105 and 109 are connected to the first electronic device 112 via interconnects 196 and 198. In a representative embodiment, each electrode 105 and 109 is coupled to a transducer via the interconnects 196 and 198. The interconnects 196 and 198 may be disposed on a surface of the channel 140 via printing or additive manufacturing, or they may comprise conventional wiring. In one embodiment, the interconnects 196 and 198 include a flex substrate. Additive manufacturing of interconnects 196 and 198 allows additional layers to be placed over the interconnects 196 and 198 to insulate the interconnects and thereby provide electrical and environmental protection. In one embodiment, direct write/printed silver interconnects and pads are covered with a polymer layer on a metallic conductor. Additive manufacturing techniques may also be used to print dedicated electrodes on transducers to provide wave control. In addition, additive manufacturing may simplify assembly of transducers by printing lateral electrical pads for connection. In one embodiment, direct write/printed electrical interconnects are covered with a polymer layer on a flexible structure.

Figure 4:
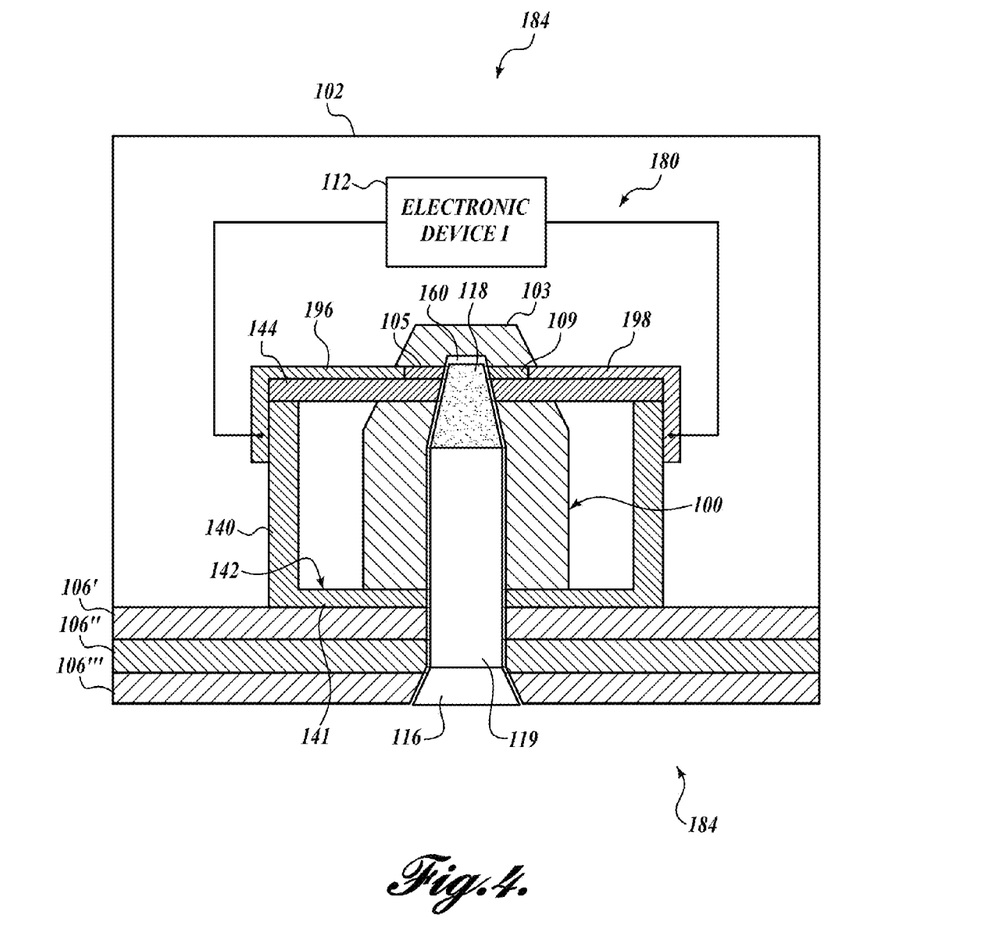
FIG. 4 is schematic diagram of a fastener hole connection system with a fastener mated with a socket in accordance with one or more embodiments of the present disclosure.

FIG. 4 shows a fastener hole connection system 100 in a fastener configuration. The fastener hole connection system 100 includes the socket 103, a system fastener 119, and a plug 200 (shown in FIG. 5). The system fastener 119 is a device that mechanically joins or affixes two or more objects. The system fastener 119 may include a bolt, a rivet, a screw, an insert, a pin, a pipe plug, a bit, an anchor, an insert, a threaded rod, a pin fastener, a blind fastener, a threaded fastener, studs, and retaining rings. It will also be appreciated that other types of fasteners may be practiced with embodiments of the present disclosure. The system fastener 119 may have comparable strength properties and similar fastening and joining capabilities as the standard fastener shown in FIG. 2. The system fastener 119 has an end 116 that has a radius that is wider than the radius of the hole 160.

In FIG. 4, the system fastener 119 has been inserted into the hole 160 and mated with the socket 103. In one embodiment, a standard fastener such as the fastener shown in FIG. 2, may be mated with the socket 103 to mechanically join or affix surfaces between one or more layers 106', 106", 106'". The layers 106', 106", 106'" may include such parts as beams, skins, doublers, laminators, ribs, nut plates or any other type of structural or non-structural member. As used in connection with a fastener, mating refers to a mechanical coupling between two objects, such as a fastener and a compatible socket. If the system fastener 119 is a threaded-type, then the socket 103 may include compatible threading, and the system fastener 119 may be mated with the socket 103 via the compatible threading. In addition to joining or affixing two or more objects, the system fastener 119 may also provide additional functionality related to protecting, covering, or sealing the hole 160.

Figure 5:
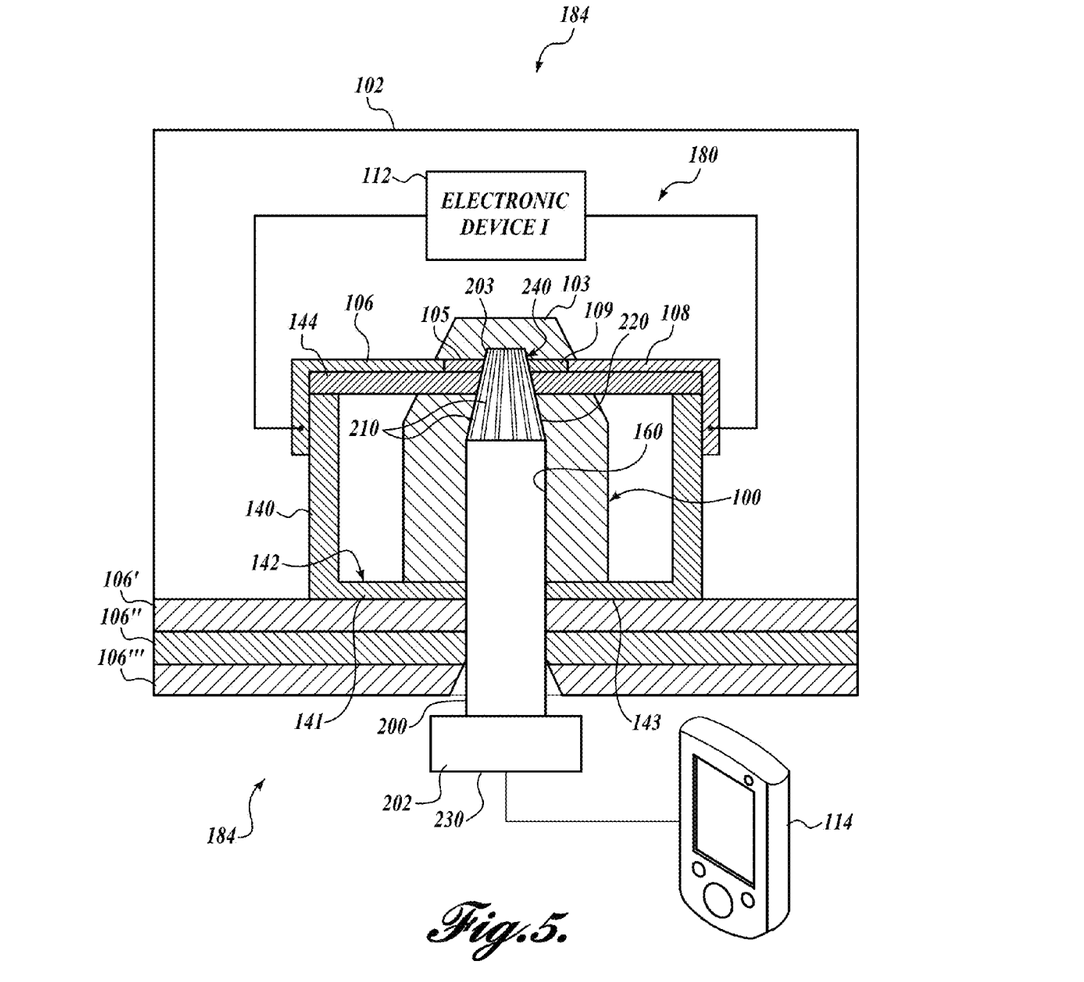
FIG. 5 is schematic diagram of a fastener hole connection system with a plug mated with a socket in accordance with one or more embodiments of the present disclosure.

Referring now to FIG. 5, the fastener hole connection system 100 is shown in a plug configuration. The sealing fastener 119 that was depicted as mated with the socket 103 in FIG. 4 has been removed from the hole 160, and a plug 200 has been inserted into the hole 160. The plug 200 is shown as mated with the socket 103. The plug 200 has a top end 220 and a bottom end 230. As shown, the plug 200 extends through the layers 106', 106", and 106'". A plurality of contacts 210 are disposed on an outer surface 240 of the top end 220 of the plug 200. When the plug 200 is mated with the socket 103, the contacts 210 are coupled to the electrodes 105 and/or 109. The socket 103 and the plug 200 may be sized and configured to electrically couple the one or more electrodes 105 and 109 through the contacts 210 when the socket 103 and the plug 200 are mated. The electrical coupling is obtained by direct or indirect electrical contact between the contacts 210 and the electrode 105 or 109. In one embodiment, an intermediary conductive material may be disposed between the contacts 210 and the electrodes 105 or 109. The mating between the plug 200 and the socket 103, and correspondingly, the contacts 210 and electrodes 105 and 109 may be performed manually by an operator using a hand to hold the bottom end 230 of the plug 200 at the handle 202 and extending the top end 220 of the plug 200 through the hole 160 until the direct or indirect contact has occurred. It general, it is desirable to mate the plug 200 and socket 103 when the fastener hole connection system 100 is stationary.

In a representative embodiment, mating between the plug 200 and the socket 203 involves an operator or a device exerting a force against the bottom end 230 of the plug 200, thereby inserting the top end 220 into the hole 160 so that the outer surface 240 of the plug 200 is adjacent to the socket 103. The force moves the contacts 210 towards the electrodes 105 or 109. An electrical connection is formed between the plug 200 and the socket 103 when the contacts 210 make direct or indirect contact with the electrodes 105 or 109. The plug 200 may be configured such that the hole 160 guides the contacts 210 towards the electrodes 105 and 109. The socket 103 or electrodes 105 and 109 may be configured to indicated to an operator that the electrical coupling between the contacts 210 and electrodes 105 and 109 has occurred, for example, the operator may not be able to further insert the plug 200 into the hole 160 once the contacts 210 are in contact with the electrodes 105 and 109.

A fixing element 144 may be provided. The fixing element 144 may be any device or structure that helps to form a connection between the contacts 210 and the electrodes 105 or 109 or retain the plug 200 when it has been mated with the socket 103. In one embodiment, the fixing element 144 physically maintains the contacts 210 at a desired position relative to the electrodes 105 or 109. In one embodiment, the fixing element 144 is a clip that uses a spring to apply pressure to the plug 200 to retain the plug in the socket 103. The fixing element 144 may include a resilient material that may deform and hold the electrodes 105 and 109 in a desired position. In a representative embodiment, the plug 200 is configured to be immobilized when mated with the socket 103. In a representative embodiment, the fixing element 144 is sized and configured to allow the contacts 210 to mate with the electrodes 105 and 109 without requiring that an operator hold the plug 200 in place. The fixing element 144 may be configured to anchor the plug 200 when the plug has been mated to the electrodes 105 and 109.

The fixing element 144 may also prevent or enable a connection between one or more particular contacts 210 and the one or more electrodes 105 and 109. In some embodiments, a plug 200 and a socket 103 may be capable of multiple mating orientations. In one embodiment, matching particular contacts 210 with the electrodes 105 or 109 is done manually by an operator. However, it may be desirable to prevent or ensure a particular mating orientation between the plug 200 and socket 103. For example, if an incorrect mating orientation is used, it may result in a power signal being input into an output of the first electronic device 112, which could damage the device. In a representative embodiment, the fixing element 144 is a groove that requires a plug having a matching notch be inserted into the hole 160. The matching groove and notch ensures that the plug 200 is mated in a particular orientation that matches one or more contacts 210 with one of the electrodes 105 and 109. Matching a particular contact 210 with a particular electrode 105 or 109 reduces the likelihood of measurement errors or damage to the fastener hole connection system 100, first electronic device 212, and other connected devices.

The fixing element 144 may be located directly above or level with the top end 220 of the plug 200. The fixing element 144 may be disposed within the socket 103 such that the plug 200 contacts the fixing element 144 adjacent to the contacts 210. In one embodiment, the plug 200 may contact the fixing element 144 at a tip. In one embodiment, the plug 200 and the socket 103 include a matching pin and slot. In such an embodiment, the pin must be aligned with the slot in order for the plug 200 and socket 103 to be mated, thereby ensuring that a particular combination of electrodes and contacts are mated.

The plug 200 may include a handle 202. The handle 202 may be on the bottom end 230 of the plug 200. The handle 202 may be configured to provide structural support and interface to other electronic devices. The plug 200 may be coupled to the I/O device 110 through the plug 200. The I/O device 110 may be any suitable electronic device for electrically coupling with the plug 200. The I/O device 110 may include a compatible digital test tool, storage device, power supply, signal generator, controller, table computer, PC, personal digital assistant, or smartphone. In one embodiment, the I/O device 110 is a signal analyzer. The I/O device may be coupled to the plug 200 through a suitable port disposed in the handle 202. The I/O device may control the first electronic device 112 or receive data from the first electronic device 112 through the hole 160 via a connection between the contacts 210 and the electrodes 105 and 109.

In one embodiment, the plug 200 is further configured to pass one or more driving signals received from the I/O device 110 through the one or more electrodes 105 and 109 to the first electronic device 112. Similarly, the plug 200 may be configured to pass one or more electrical signals from the first electronic device 112 through the one or more electrodes 105 and 109 to the I/O device 110. The plug 200 may be configured to pass one or more electrical signals from the first transducer through the one or more electrodes 105 and 109 to the I/O device 110.

Figures 6, 7:
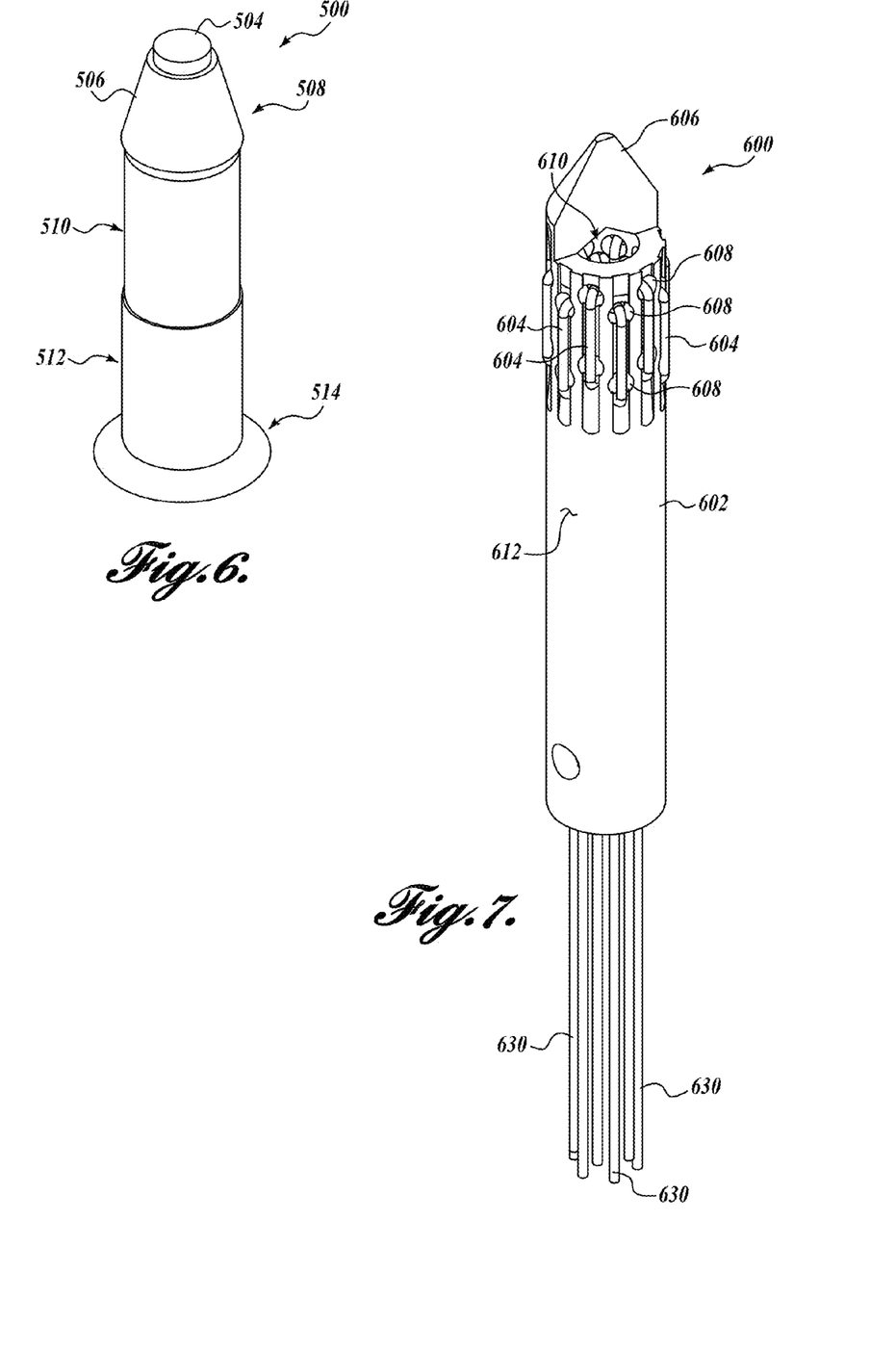
FIG. 6 illustrates a front top perspective view of an embodiment of a system fastener that is suitable for use with the fastener hole connection system of the present disclosure.
FIG. 7 illustrates a front top perspective view of an embodiment of a plug that is suitable for use with the fastener hole system of the present disclosure.

Referring now to FIG. 6, a representative embodiment of a system fastener 500 that may be suitable for use with the fastener hole connection system 100 in the fastener configuration is provided. The system fastener 500 has a first portion 508, a second portion 512, and a third portion 510. The third portion 510 is disposed between the first portion 508 and the second portion 512. The first portion 508 terminates at a first end 504 and the second portion 512 terminates at a second end 514. One or more of the first portion 508, middle portion 510, and bottom portion 512 of the system fastener 500 may have a cylindrical shape.

The first portion 508 of the system fastener 500 includes a cap 506. The cap 506 may include a resilient material, such as a silicone material. The cap 506 may have a cylindrical shape. As shown in FIG. 5, the cap 506 may be tapered. The cap 506 is sized and configured to provide protection for one or more electrodes 105 or 109 located adjacent to the cap 506 when the system fastener 500 is inserted into the socket 103 and mated therewith. In addition, the cap 506 is sized and configured to cover the one or more electrodes 105 or 109 or the socket 103 to protect from moisture or debris.

Figure 10:
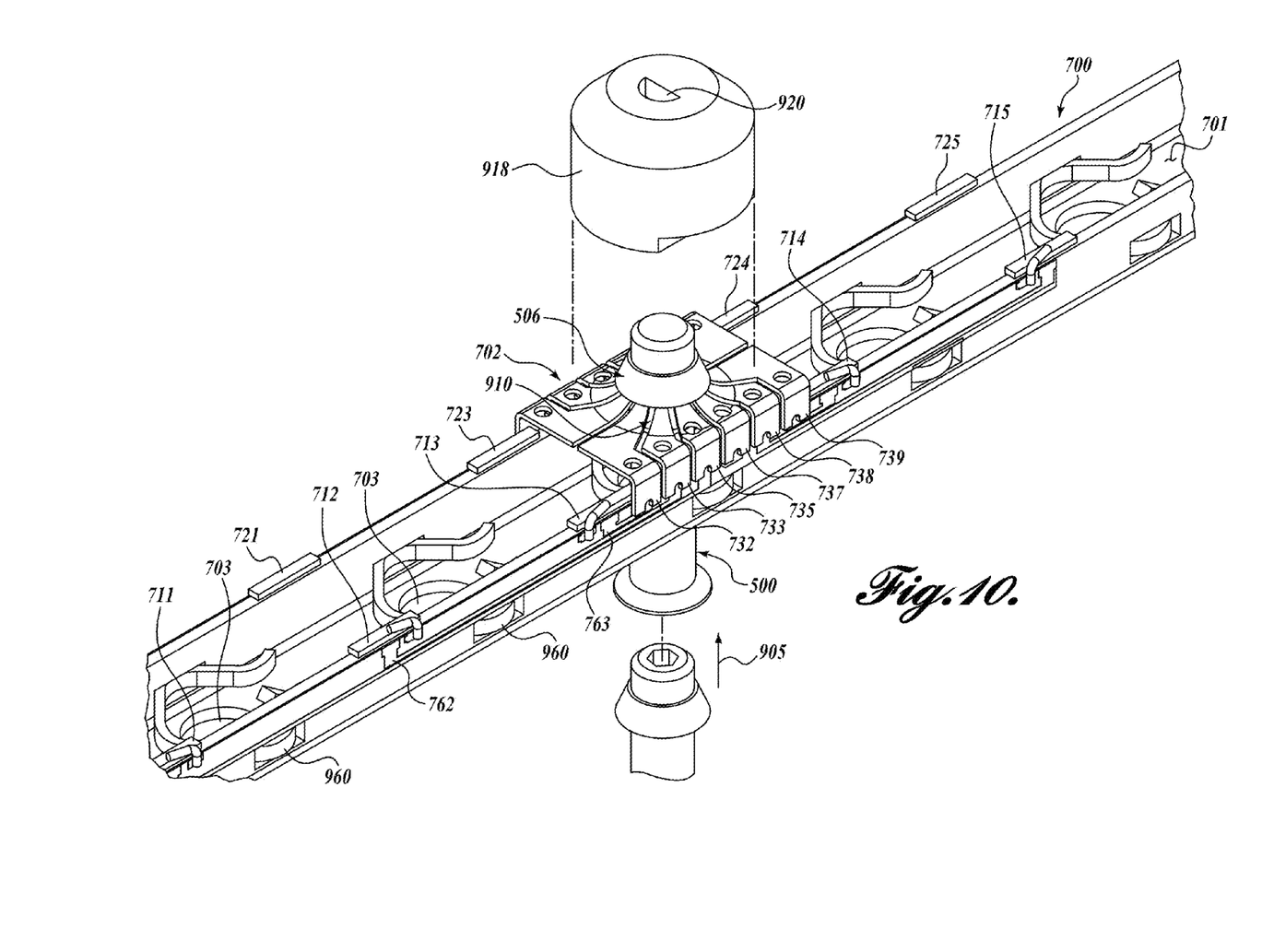
FIG. 10 illustrates a top perspective view of an embodiment of a system fastener that is coupled to a socket in accordance with one or more embodiments of the present disclosure.

Covering the hole 160 may prevent damage or corrosion to the electrodes 105 or 109 and socket 103, among other benefits. The fastener 500 may be sized and configured such that the cap 506 makes contact with the one or more of the electrodes, such as the electrodes 105 and 109, when the system fastener 500 is mated with the socket 103. In a representative embodiment, the cap 504 is sized and configured to deform in response to contacting an electrode. In a representative embodiment, the cap 504 is configured to make contact with and deform around the one or more electrodes when the fastener is mated with the socket. The cap 504 may deform such that its diameter extends to cover the hole 160 and thereby separate an outside space from the electrodes 105 and 109. In one embodiment, the resilient material is configured to deform and seal the hole 160 when the system fastener 500 is mated with the socket 103. The resilient material may include an inner end and an outer end that deforms around the one or more electrodes 105 and 109, as shown in FIG. 10.

The system fastener 500 may include similar materials as a standard fastener, such as the fastener shown in FIG. 2. If a fastener without the cap 506 is utilized when practicing embodiments of the present disclosure, similar fastening and joining properties may be realized; however, the electrodes may not be covered or protected due to the absence of the cap 506. Protecting and sealing the electrodes 105 and 109 may help to prevent corrosion to and debris from adhering to the electrodes 105 and 109 and thereby interfere with the forming of electrical connections at the electrodes 105 and 109.

Referring now to FIG. 7, an embodiment of a plug 600 that may be suitable for use with the fastener hole connection system 100 is provided. The plug 600 is sized and configured such that it may be mated with the socket 103. The plug 600 includes a plug body 602 and one or more contacts 604. The plug body 602 has an outer surface 612. The plug body 602 may include an insulator material, such as a plastic or composite material, and have a cylindrical shape. The plug body 602 may include an elongated portion in the transverse direction of the plug body 502. The plug body 602 also includes a plurality of hole pairs 608 that are disposed on the outer surface 612.

The contacts 604 are disposed adjacent to the outer surface 612 of the plug body 602. The contacts 604 may extend into the plug body 602 at one or both of the hole pairs 608. In one embodiment, the contacts 604 are disposed onto the outer surface 612 of the plug body 602. The contacts 604 include a conductive material and may also include an insulator material. A conductive material may be exposed on an outer-facing surface of the contact 604 with respect to the plug body 602 such that the contact 604 may form an electrical connection (electrical coupling) with an electrode when placed in contact with the electrode. In one embodiment, one or more of the contacts 604 include a portion having a flat shape that is adjacent to the outer surface 612 of the plug body 602. One or more of the contacts 604 may include a rigid material. The rigid material helps to maintain a contact pressure between a contact and an electrode to ensure an electrical connection. In addition, the rigid material prevents the contact 604 from bending in response to contact with an electrode.

The contacts 604 may be coupled to or include wires 630. The wires 630 may be located within the plug body 602. In one embodiment, the contacts 604 include the wires 630. The wires 630 may be accessible from the plug body 602 when the plug 600 has been mated with a socket 103. In one embodiment, the wires 630 are coupled to an electrical connector that is embedded within the body 602. In a representative embodiment, the plug 600 includes a handle, and the connector is included in the handle. In one embodiment, the wires 630 are directly connected to a device that is located outside of the plug body 602. In one embodiment, the wires 630 are connected to a module capable of transmitting and receiving electrical signals wirelessly thereby allowing electrical coupling between the plug 600 and a device.

The plug 600 includes a tip 606 that is sized and configured to prevent mating between a plug 600 and an incompatible socket 103. The tip 606 may also be sized and configured to limit the possible orientations in which the plug 600 may be mated with a socket 103. In particular, a socket 103 that is compatible with the plug 600 would include a recess shape matched to receive the tip 606. In order for the plug 600 to be mated with the compatible socket 103, the tip 606 and the recess of the socket 103 must be aligned. Other combinations such as matched pairs of notches and grooves between a plug 600 and compatible socket 103 can be used to ensure that the socket 103 and plug 600 are mated in a particular orientation. Without the tip 606, the plug 600 could potentially be mated with the socket 103 in multiple orientations. It may be desirable to limit one or more of the contacts 604 to electrical coupling with one or more particular electrodes 105 or 109.

Figure 8:
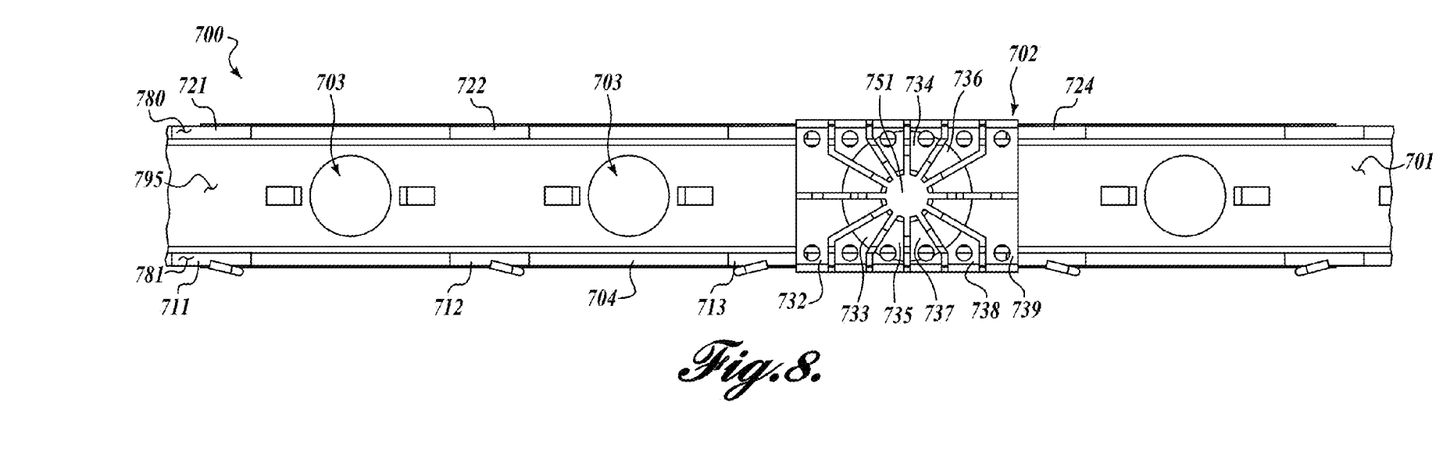
FIG. 8 illustrates a top plan view of an embodiment of electrodes, transducers, and a channel that is suitable for use with one or more embodiments of the present disclosure.

Referring now to FIG. 8, a top view of a mounting plate 700 is provided. The mounting plate 700 includes a channel 701 defined by a first side 780 and a second side 781 that extend perpendicular from a bottom surface 795 of the mounting plate 700. The mounting plate 700 includes a first plurality of transducers 721, 722, 723, 724, and 725 that are disposed on the first side 780 of the channel. A second plurality of transducers 711, 712, 713, 714, and 715 are disposed on the second side 781 of the channel. An electrode arrangement 702 includes a plurality of electrodes 732, 733, 735, 737, 738, 739 that originate around a hole 751 centered between the first side 780 and the second side 781 and that extend radially outward away from the hole 751 until they terminate at either the first side 780 or the second side 781 of the channel 701. Openings 703 allow for fastener hole connection systems 100 or standard fasteners and sockets to be incorporated into the channel 701.

Figure 9:
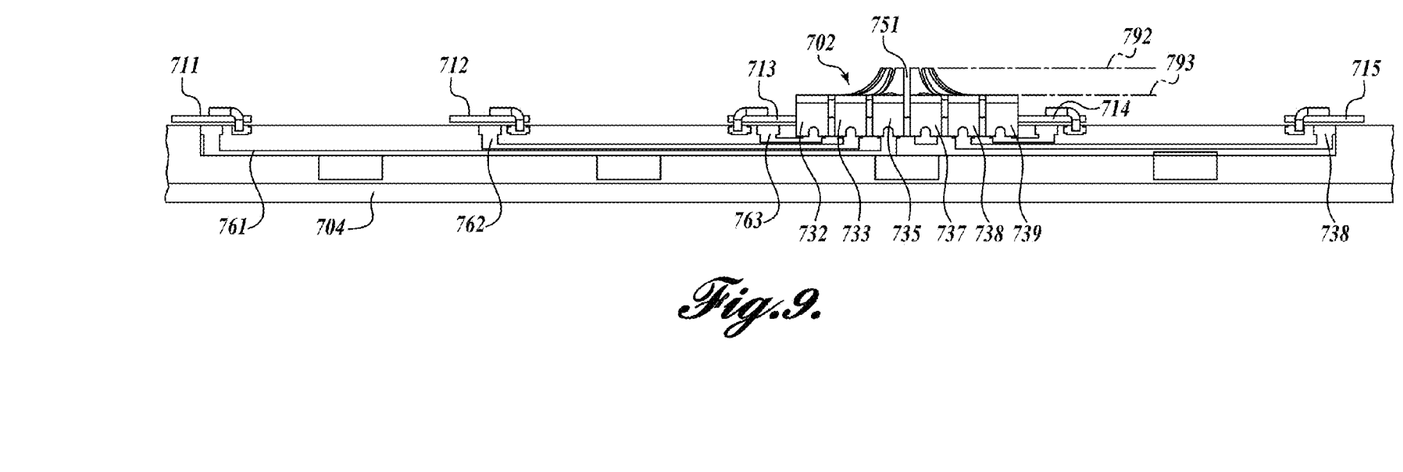
FIG. 9 illustrates a side elevation view of electrodes, transducers, and a channel that is suitable for use with one or more embodiments of the present disclosure.

FIG. 9 depicts a side view of the second side 781 of the mounting plate 700 and an electrode arrangement 702 that includes a plurality of electrodes 732, 733, 735, 737, 738, 739. The plurality of electrodes 732, 733, 735, 737, 738, 739 originate at a first plane 792 that is higher than a second plane 793 with respect to a channel bottom 704. The second plane 793 is defined by the height of the first side 790 or the second side 791. As the electrodes 732, 733, 735, 737, 738, 739 extend away from the hole 751, they pass from the first plane 792 towards the second plane 793. Just above the second plane 793, the plurality of electrodes 732, 733, 735, 737, 738, 739 extend parallel to the bottom surface 795 of the channel 701. At about the first side 780 or the second side 781, each electrode bends approximately 90 degrees and terminates at an adjacent outward facing side. At the point of termination, each electrode may be coupled to an interconnect. For example, electrode 732 is coupled to the transducer 711 via an interconnect 763. Electrode 733 is coupled to the transducer 712 via an interconnect 762. Electrode 735 is coupled to the transducer 711 via an interconnect 761. The electrode arrangement 702 is a radial type arrangement. The electrode arrangement 702 may be compatible for use with plug 600 and system fastener 500 and the fastener hole connection systems 100.

FIG. 10 depicts a mounting plate 700, electrode arrangement 702, and a system fastener 500. The system fastener 500 has been vertically inserted from below the mounting plate 700 in a direction 905. The fastener cap 506 is deforming at junction 910 in response to contact by the electrode arrangement 702. This deforming of the fastener cap 506 may protect the electrodes configuration 702 from debris or moisture that could enter from the hole 160 (not shown). A housing 918 is also provided for covering the electrode arrangement 702. A positioning casting 960 may secure a socket 103 or standard nut socket in the channel 140.

The electrode arrangement 702 is also suitable for use with the plug 600. The housing 918 includes a notch 920 that may be used as a fixing element 144 in the fastener hole connection system 100. The notch 920 and the tip 606 may be configured to anchor the plug 600 when the plug 600 and the socket 103 have been mated. The plug 606 may be anchored using the fixing element 144. In addition, a positioning of the notch 920 relative to the electrode arrangement 702 determines a mating orientation between the socket 103 and the plug 600 because the tip 606 of the plug 600 must be aligned with the notch 920 for mating to occur. In some embodiments, inserting the tip 606 into the notch 920 may also retain the plug 600 in the socket 103.

Figure 11:
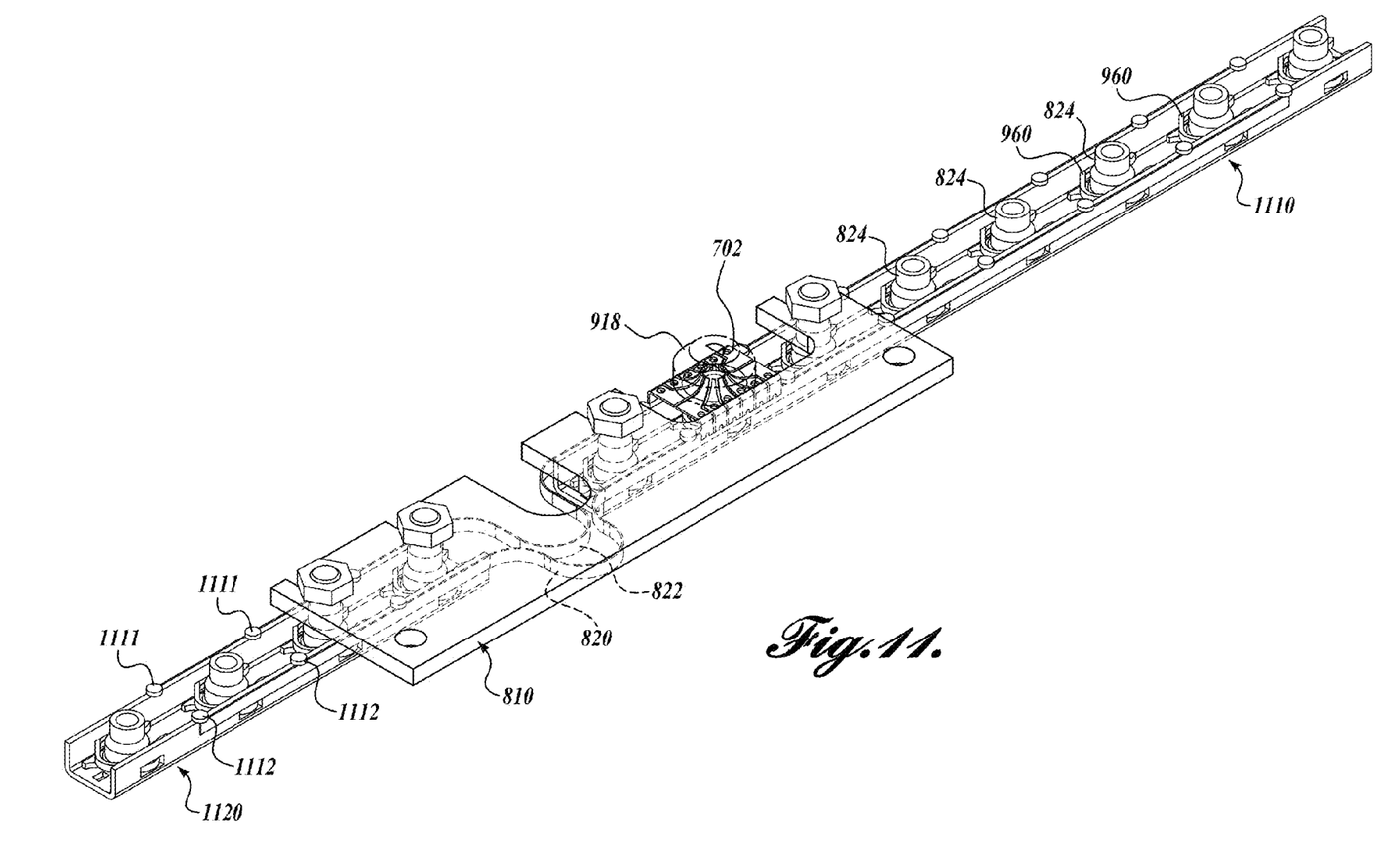
FIG. 11 illustrates a top perspective view of an embodiment of a system fastener that is coupled to a socket in accordance with one or more embodiments of the present disclosure.

FIG. 11 depicts an embodiment of a first nut plate 1110 that includes the electrode arrangement 702 and the housing 918. The electrode arrangement 702 is coupled to a first flexible connector 820 and a second flexible connector 822. The first flexible connector 820 is coupled to a plurality of first transducers 1111. The second flexible connector 822 is coupled to a plurality of second transducers 1112. The first transducers 1111 and the second transducers 1112 are mounted on a second nut plate 1120. A support element 810 may be provided to support the first nut plate 1110 and the second nut plate 1120. The use of the first flexible connector 820 and the second flexible connector 822 allow a first electronic device 112, such as transducers, to be placed on a different structural element than where the socket 103 is located. A plurality of regular sockets 824 are each secured by a positioning casting 960 in a channel 1150. In some embodiments, the positioning casting 960 may position the socket 103 relative to the hole 160.

Figure 12:
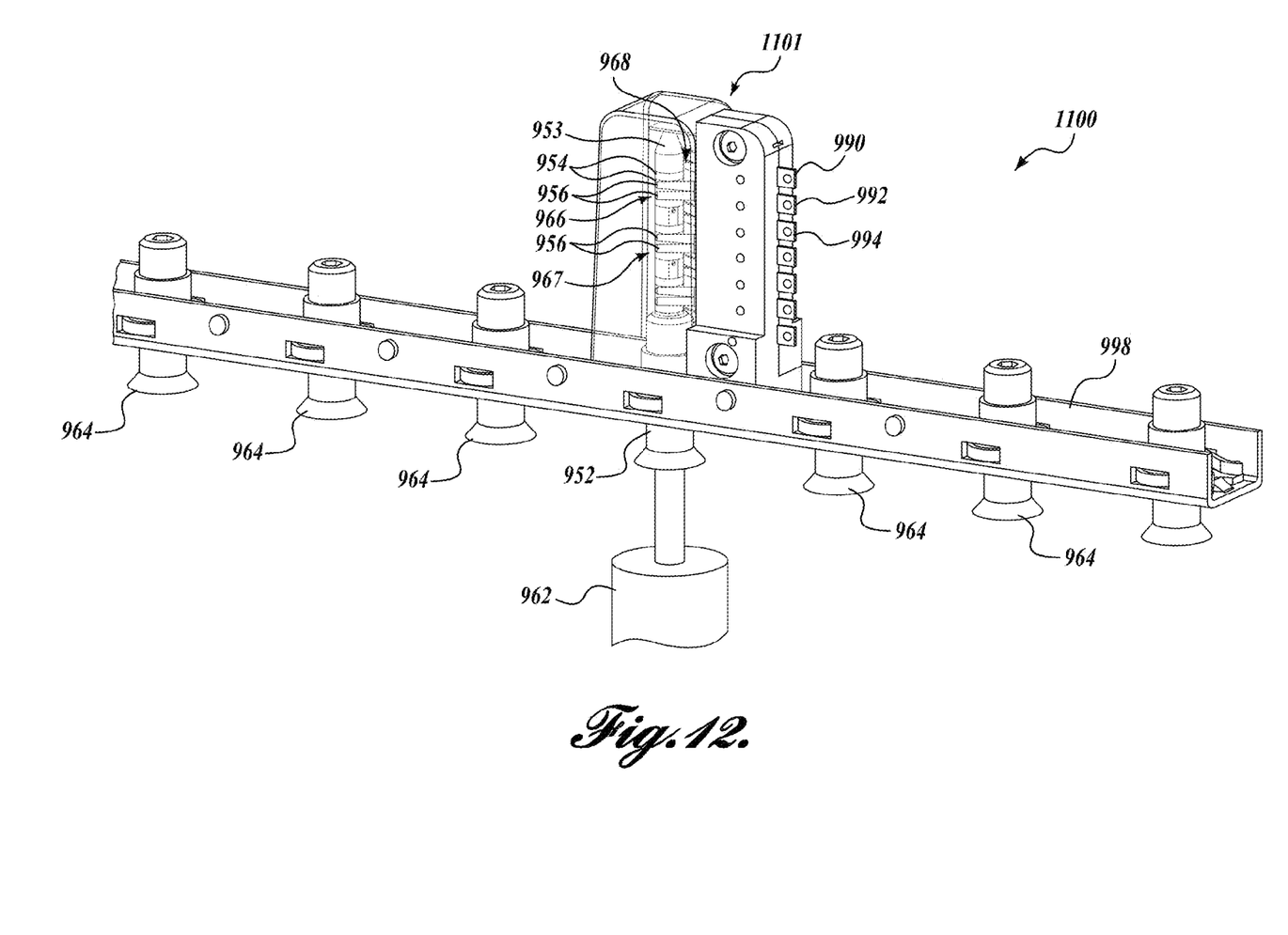
FIG. 12 illustrates a top perspective view of an embodiment of a vertical socket in accordance with one or more embodiments of the present disclosure.

FIG. 12 depicts an embodiment of the fastener hole connection system 100 on a nut plate 998 that uses a vertical connector socket 1101. A plurality of fastener socket mated pairs 964 are included in the nut plate 998. The mated pairs 964 are located adjacent to the vertical connector socket 1101. A plug 952 with a handle 962 has been coupled to the vertical socket connector 1101. A top portion 953 of the plug 952 is positioned adjacent to the vertical connector socket 1101. The top portion 953 includes a plurality of contacts 954. The vertical connector socket 1101 includes a plurality of electrodes 956. The electrodes 956 form electrical connections with the contacts 954 at the contact points 966, 967, and 968. The electrodes 956 are coupled to interface points 990, 992, and 994. Interface points 990, 992, and 994 may be electrically coupled to an electronic device such as the first electronic device 112.

Figure 13:
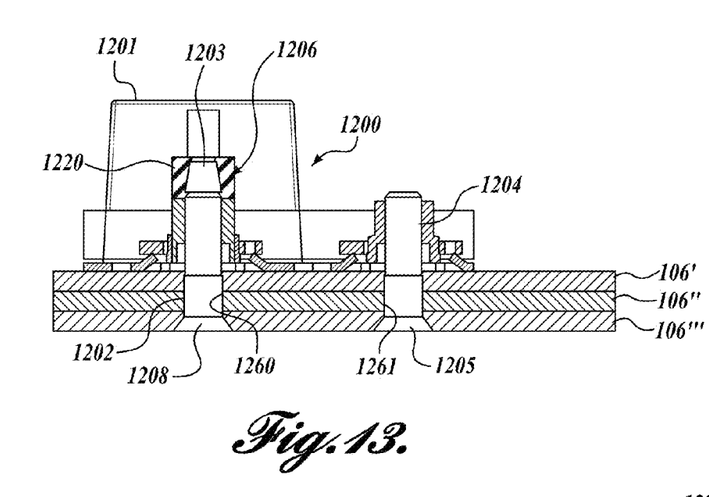
FIG. 13 illustrates a side elevation view of an embodiment of a system fastener mated with a socket and an adjacent standard fastener mated with a standard socket in accordance with one or more embodiments of the present disclosure.

FIG. 13 shows a fastener connector system 1200 within a closed space that includes a system fastener 1202 that has been mated to a socket 1220. A cap 1203 of the system fastener 1202 is deformed within the socket 1220 at a contact point 1206 to protect the socket 1220 from moisture or debris from an external space. In addition, a housing 1201 may be provided to protect the socket 1220 from moisture or debris within the internal space. The mating between the system fastener 1202 and the socket 1220 creates a joining force that is applied to the layers 106', 106", and 106'''. A regular fastener 1205 and a regular socket 1204 are located adjacent to the fastener connector system 1200. The mating between the regular fastener 1205 and the regular socket 1204 also creates a joining force that is applied to the layers 106', 106", and 106'''. The system fastener extends through a first hole 1260 and the regular fastener passes through a second hole 1261. The first hole 1260 and the second hole 1261 have similar dimensions, and the regular socket 1204 and the socket 220 may be switched, or the socket 220 may be replaced with a regular socket 1204.

Figure 14:
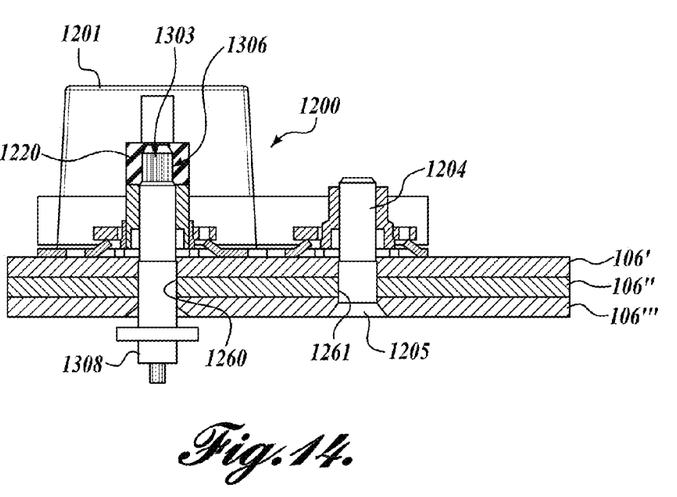
FIG. 14 illustrates a side perspective view of an embodiment of a plug mated with a socket and an adjacent standard fastener mated with a standard socket in accordance with one or more embodiments of the present disclosure.

FIG. 14 shows a fastener connector system 1200 that includes a plug 1308 that has been mated with the socket 1220. The socket 1220 is a radial-type socket. The plug 1308 includes a plurality of contacts 1303 that are arranged such that they are compatible with the socket 1220. The contacts 1303 are electrically connected to the socket 1220 at connection points 1306. The plug 1308 and the socket 1220 form a radial-type connection.

In one aspect, an electrical connection plug is provided such as is in connection with FIGS. 3-5, 7, 12, and 13. In one embodiment, the electrical connection plug, such as plug 200, plug 600, or plug 952, is sized and configured to mate with, and thereby form an electrical connection with, one or more electrodes, such as electrodes 105 and 109, the electrodes in the electrode arrangement 702, or electrodes 956. The plug 200 should have dimensions such that the top end 220 may pass through the hole 160 allowing the top end 220 to move from the exterior space 184 into the interior space 180. The plug 200 should be sufficiently elongated such that the contacts 210 included in the top end 220 may extend into the hole 160 and may mate with the electrodes 105 and 109 as the handle 202 remains in the exterior space 184. The contacts 210 should be positioned on the plug 200 such that they may form an electrical connection with electrodes 105 and 109 when the top end 220 of the plug 200 has been inserted through the hole 160. For example, if electrode arrangement 702 is used, the contacts 210 may be disposed such that they may form an electrical connection with one or more electrodes 105 and 109 and the electrode arrangement 702. If a radial arrangement of electrodes 105 and 109 is used, such as electrode arrangement 702, then the plug 200 may have its contacts 210 arranged radially, such as the contacts shown in FIG. 7. The electrical connection may be formed by the plug 200 and the electrodes via direct or indirect contact between the electrodes 105 and 109 and the contacts 210.

The electrodes 105 and 109 may be included within and supported by the socket 103. The socket 103 may be mounted on a channel, such as a nut plate or gong channel. The socket 103 is positioned on the channel such that it is adjacent to the hole 160. The electrodes 105 or 109 are disposed within an interior space 180 of the closed structure 102. The plug 200 is mated with the electrodes 105 or 109 when the plug 200 is inserted through the hole 160 in the closed structure 102. The closed structure may include an airplane wing, a fuselage, or an engine compartment. The hole 160 may also retain a fastener, such as the system fastener 119 or the system fastener 500. For example, the socket 103 or the hole 160 may be mated with the system fastener 119 or a regular fastener via compatible threading.

Mating the system fastener 119 or a regular fastener with the socket 103 allows the hole 160 to retain a fastener. The plug 200 is removed from the hole 160 prior to mating between a fastener and the socket 103 or the hole 160. Relatedly, the system fastener 119 is removed from the hole 160 prior to insertion of the plug 200 in the hole 160 and mating between the plug 200 and the contacts. Inserting and removing the plug 200 and the system fastener 119 into and out of the hole 160 may be performed by a person. In some embodiments, a tool or device may also be needed to insert into or remove the fastener or the plug from the hole.

In another aspect, a method of forming an electrical connection with one or more electrodes disposed within a closed structure is provided. In one embodiment, the electrodes are disposed in an interior space of the closed structure adjacent a hole, such as hole 160, hole 1260, or hole 1261, in the closed structure configured to retain a fastener, the method comprising the step of inserting an electrical connection plug, such as plug 200, plug 600, or plug 952, sized and configured to mate with the one or more electrodes through the hole until the plug forms at least one electrical contact with at least one electrode. As discussed above in connection to FIGS. 3-5, inserting the plug 200 into the hole 160 may be accomplished by an operator holding the bottom end 230 of the plug 200 at the handle 202 and moving the plug 200 such that the top end 220 is moved into the hole 160 towards the electrodes 105 such that the contacts 210 and the electrodes 105 and 109 become directly or indirectly engaged. In one embodiment, a fastener is removed prior to the insertion of the plug 200. When an electrical connection has been formed between the plug 200 and the electrodes 105, an electrical signal may be applied to the electrodes 105 and 109 via the plug 200 from the electronic I/O device 110. The electrical signal may be a driving signal or a command signal to instruct the first electronic device to generate a particular signal. Relatedly, the electronic I/O device may also receive signals from the first electronic device 112 via the electrodes, when the plug 200 and the electrodes have formed an electrical connection. For example, the I/O device may be received a signal from a receiving device included in the first electronic device 112.

After a plug 200 has been inserted in the socket 103, the plug be removed from the socket 103. The plug 200 may be removed by moving the plug in an opposite direction that was used to insert the plug 200 in the socket, e.g., the plug 200 may be removed through the hole 160. Removal may be performed by an operator. When the plug 200 is removed, it is no longer in the closed space 102. When the plug 200 is removed, the plug 200 is no longer in contact with the electrodes 105 and 109. When the plug 200 is not in the hole 160, the hole 160 may be covered using a fastener, a replacement fastener, an insert, or a cover. Covering may be performed by an operator. A cover may include a material affixed to an outer surface of a layer, such as layer 106''', for example. The cover prevents foreign objects from entering the hole 160. An insert may include a device that is placed in the hole 160. An insert may not need to mate with the socket 103 to be secured in the hole 160. The insert may include a wide range of materials such as plastics or resilient materials. Generally, the insert should be designed so that it does not fall during the normal use of the closed space 102 and out leave the hole 160 exposed. Other methods of protecting the hole 160 from foreign objects, such as debris or moisture, may be utilized when a plug 200 or a fastener have not been inserted in the hole.

The socket 103 is mounted adjacent to the hole 160 such that it may receive the fastener through the hole 160 and mate with the fastener. For example, the fastener may include the system fastener 119, the system fastener 500, or the regular fastener shown in FIG. 2. When mated with the socket 103, the system fastener 119 is retained in the hole 160. In some embodiments, the system fastener 119 may be retained within the closed structure 102 by mating the system fastener 119 with the hole 160. Mating between the hole 160 and the system fastener 119 may be accomplished by using compatible threading for the hole 160 and the system fastener 119.

In another aspect, a corrosion sensor network configured to test a level of corrosion of a test piece is provided. The first electronic device 112 may include the corrosion sensor network. The corrosion sensor network may include one or more transducers. The test piece may be any physical element within the closed structure 102. In the context of corrosion sensing, the test piece is any matter that is capable of corroding. The pair of sensing/acting transducers may be mounted on opposite surfaces of the test piece. For example, the test piece may include a structural element located within the closed structure 102. In one embodiment, the test piece is a portion of a mounting plate, such as a mounting plate 700, where a socket may be mounted. In one embodiment, the corrosion sensor network includes at least one pair of sensing/acting transducers positioned with the test piece in between. The transducers 713 and 723 shown in FIG. 10 may be configured as a corrosion sensor network. One of the transducers 713 and 723 may generate a signal that indicates a corrosion level of the test piece. For example, the transducers 713 and 723 may alternatively be positioned on opposite surfaces of the first side 780 of the channel 701 shown in FIGS. 8 and 9. In one embodiment, interconnects are shown connecting the at least one pair of sensing/acting transducers with an electrical I/O interface. As depicted in FIG. 10, the transducers are connected to the electrodes in the electrode arrangement 702. The electrodes of the electrode arrangement may form an I/O interface when mated with a compatible plug, such as plug 600. When the electrode arrangement 702 is mated with a compatible plug, driving or activation signals may be input to the first electronic device 112 through the plug. Such signals may be received from the electronic I/O device 110. Signals may also be output from one or more transducers through the electrodes and contacts and into the I/O device 110.

In another aspect, a system is provided. In one embodiment, the system includes: a socket that comprises one or more electrodes, wherein the one or more electrodes are electrically coupleable to a first electronic device; and a plug that is electrically coupleable to an electronic I/O device. The system could include embodiments of the fastener plug system 100 described in connection with FIGS. 3-5. The socket 103 is configured to mate exclusively through a hole with either the plug 200 or a fastener. The socket 103 may not mate with the plug 200 and the fastener at the same time due to both needing to pass through the hole 160 to mate with the socket 103 and other space constraints related to the socket 103. The socket 103 and the plug are sized and configured to electrically couple the one or more electrodes 105 and 109 through the plug 200 when the socket 103 and the plug 200 are mated. The electrical coupling is formed via an electrical connection between the contacts 210 on the plug 200 and the electrodes 105 and 109.

In one embodiment, the socket 103 is coupleable to a fastening system configured to join two surfaces of a structure when the socket is mated with the fastener. The fastening system includes system fastener 119. When the system fastener 119 is mated with the socket 103, at least two of the layers 106', 106", and 106''' or channel may be joined.

While illustrative embodiments have been illustrated and described, it will be appreciated that various changes can be made therein without departing from the spirit and scope of the claimed subject matter.

The embodiments of the invention in which an exclusive property or privilege is claimed are defined as follows:

1. An electrical connection plug sized and configured to mate with, and thereby form an electrical connection with, one or more electrodes disposed within an interior space of a closed structure by way of insertion through a hole in the closed structure, wherein the hole in the closed structure is configured to retain a fastener, and wherein the hole in the closed structure is configured to mate with the plug and form the electrical connection between the plug and the one or more electrodes when the fastener is not in the hole.

2. The plug of claim 1, wherein the hole in the closed structure is configured to retain one or more of a bolt, a rivet, a screw, an insert, a pin, a pipe plug, a bit, an anchor, an insert, a threaded rod, a pin fastener, a blind fastener, a threaded fastener, a stud, a retaining ring, or a special-purpose fastener.

3. The plug of claim 1, wherein the one or more electrodes are coupled to a sensor network or excitation device located inside the closed structure.

4. The plug of claim 1, wherein the plug is sized and configured to be anchored when mated with the one or more electrodes.

5. The plug of claim 1, wherein the plug is configured to electrically couple the one or more electrodes to an electronic I/O device.

6. The plug of claim 5, wherein the plug is further configured to pass one or more driving signals from the electronic I/O device through the one or more electrodes to a sensor network comprising at least a first transducer and a second transducer, defining a pair of transducers, wherein the sensor network is located in the closed structure.

7. The plug of claim 6, wherein the plug is configured to pass one or more electrical signals from the first transducer through the one or more electrodes to the electronic I/O device.

8. The plug of claim 7, wherein the one or more electrical signals are generated by the first transducer in response to the second transducer receiving the one or more driving signals passed from the electronic I/O device.

9. The plug of claim 7, wherein the signal generated by the first transducer indicates a corrosion level of a test piece located between the pair of transducers.

10. A corrosion sensor network configured to test a level of corrosion of a test piece, comprising:
  at least one pair of sensing/acting transducers positioned with the test piece in between, wherein the test piece is included or located within a closed structure; and
  interconnects connecting the at least one pair of sensing/acting transducers with one or more electrodes disposed within an interior space of the closed structure, wherein the one or more electrodes are accessible via a hole in the closed structure, wherein the hole in the closed structure is configured to retain a fastener, and wherein the hole in the closed structure is configured to mate with the plug and form an electrical connection between the plug and the one or more electrodes when the fastener is not in the hole.

11. The corrosion sensor network of claim 10, wherein the interconnects are formed using additive manufacturing.

12. The corrosion sensor network of claim 10, wherein the sensing/acting transducers include an electrode formed using additive manufacturing.

13. The corrosion sensor network of claim 10, wherein the corrosion sensor network is disposed within the closed structure.

14. The corrosion sensor network of claim 10, wherein the closed structure comprises at least one fastener inserted through the hole in order to apply a joining force between two surfaces that form the closed structure, and wherein the corrosion sensor network further comprises an electrical I/O interface disposed adjacent to the hole in the closed structure such that the electrical connection plug is configured to electrically couple the electrical I/O interface to the one or more electrodes in the hole when the fastener is removed from the hole.

15. The corrosion sensor network of claim 10, wherein the electrical I/O interface is configured to mate with the electrical connection plug.

16. The corrosion sensor network of claim 10, wherein the electrical I/O interface is configured to mate with a fastener.

17. A system comprising:
a socket in a closed structure, wherein the socket comprises one or more electrodes that are electrically coupleable to a first electronic device located within the closed structure; and
a plug that is electrically coupleable to an electronic I/O electronic device,
wherein the socket is configured to be mated with a fastener such that the socket is covered and unable to receive the plug when the socket is mated with the fastener,
wherein the socket is further configured to mate with the plug, wherein the socket and the plug are sized and configured to electrically couple the one or more electrodes to the plug when the socket and the plug are mated and the fastener is not in the socket, and
wherein the socket is coupleable to a fastening system which includes the fastener, wherein the fastening system is configured to join two surfaces of the closed structure when the socket is mated with the fastener.

18. The system of claim 17, wherein the first electronic device comprises a sensor network.

19. The system of claim 18, wherein the sensor network comprises a temperature sensor.

20. The system of claim 17, wherein the first electronic device comprises an excitation device configured to generate one or more of the following signals: electrical, mechanical, thermal, magnetic, optical, electromagnetic, acoustical, or ultrasonic.

21. The system of claim 17, wherein the first electronic device comprises a receiving device configured to detect one or more of the following signals: electrical, mechanical, thermal, magnetic, optical, electromagnetic, acoustical, or ultrasonic.

22. The system of claim 18, wherein the first electronic device comprises an excitation device configured to generate one or more of the following signals: electrical, mechanical, thermal, magnetic, optical, electromagnetic, acoustical, or ultrasonic.

23. The system of claim 17, wherein the electronic I/O device is a signal analyzer.

24. The system of claim 17, wherein the plug is configured to be anchored when mated with the socket.

25. The system of claim 17, further comprising:
a fastener comprising a resilient material on an end, wherein the resilient material is configured to deform and seal the socket when the fastener is mated with the socket.

26. The system of claim 25, wherein the resilient material comprises an inner end and an outer end, wherein the inner end comprises a resilient material configured to contact and deform around the one or more electrodes when the fastener is mated with the socket.

\* \* \* \* \*